United States Patent
Labhasetwar (10) Patent No.: US 12,409,147 B2
(45) Date of Patent: Sep. 9, 2025

(54) THROMBOLYTIC AND NEURO/VASCULOPROTECTIVE NANOCONJUGATES

(71) Applicant: The Cleveland Clinic Foundation, Cleveland, OH (US)

(72) Inventor: Vinod Labhasetwar, Solon, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 728 days.

(21) Appl. No.: 17/605,422

(22) PCT Filed: Apr. 22, 2020

(86) PCT No.: PCT/US2020/029205
§ 371 (c)(1),
(2) Date: Oct. 21, 2021

(87) PCT Pub. No.: WO2020/219483
PCT Pub. Date: Oct. 29, 2020

(65) Prior Publication Data
US 2022/0211634 A1    Jul. 7, 2022

Related U.S. Application Data

(60) Provisional application No. 62/837,980, filed on Apr. 24, 2019.

(51) Int. Cl.
*A61K 9/51*      (2006.01)
*A61K 38/44*     (2006.01)
*A61K 38/48*     (2006.01)

(52) U.S. Cl.
CPC .......... *A61K 9/5153* (2013.01); *A61K 38/446* (2013.01); *A61K 38/482* (2013.01);
(Continued)

(58) Field of Classification Search
CPC .. A61K 9/5153; A61K 38/446; A61K 38/482; A61K 9/0019; A61K 9/19;
(Continued)

(56) References Cited

U.S. PATENT DOCUMENTS

2006/0067925 A1    3/2006  Labhasetwar et al.
2015/0064267 A1    3/2015  Ramamurthi et al.
2016/0263148 A1*   9/2016  Pun .......................... A61P 7/00

FOREIGN PATENT DOCUMENTS

WO    WO 2014/124142    8/2014
WO    WO 2017/177134    10/2017
WO    WO 2020/219483    10/2020

OTHER PUBLICATIONS

Chung et al, "Accelerating thrombolysis with chitosan-coated plasminogen activators encapsulated in poly-(lactide-co-glycolide) (PLGA) nanoparticles", Biomat, 2008, vol. 29, Issue 2, pp. 228-237 (Year: 2008).*

(Continued)

*Primary Examiner* — Marianne C Seidel
*Assistant Examiner* — Joshua A Atkinson
(74) *Attorney, Agent, or Firm* — Jason R. Bond; Casimir Jones, S.C.

(57) ABSTRACT

Provided herein are compositions, systems, kits, and methods for treating a patient with a thromboembolism by administering nanoconjugates comprising nanoparticles encapsulating and/or conjugated to: i) tissue-type plasminogen activator (tPA), and ii) at least one antioxidant enzyme selected from the group consisting of: superoxide dismutase, glutathione peroxidase, glutathione reductase, and a catalase.

3 Claims, 5 Drawing Sheets

(52) U.S. Cl.
CPC ............... *C12Y 108/01007* (2013.01); *C12Y 111/01006* (2013.01); *C12Y 111/01009* (2013.01); *C12Y 115/01001* (2013.01); *C12Y 304/21068* (2013.01)

(58) Field of Classification Search
CPC ............... A61K 47/6937; A61K 38/44; C12Y 108/01007; C12Y 111/01006; C12Y 111/01009; C12Y 115/01001; C12Y 304/21068; A61P 9/10; C12N 9/0004; C12N 9/6459
See application file for complete search history.

(56) References Cited

OTHER PUBLICATIONS

Lapchak et al, "Ebselen, a Seleno-Organic Antioxidant, Is Neuroprotective After Embolic Strokes in Rabbits", Stroke, 2003, pp. 2013-2018 (Year: 2003).*

Khanal et al, "pH-Responsive PLGA Nanoparticle for Controlled Payload Delivery of Diclofenac Sodium", Jour Functional Biomat, 2016, 7, 21, pp. 1-12 (Year: 2016).*

Liu et al, "Tissue plasminogen activator-based nanothrombolysis for ischemic stroke", Expert Opinion on Drug Delivery, 2018, vol. 15, No. 2, pp. 173-184, first published 2017 (Year: 2017).*

Lees et al, "Time to treatment with intravenous alteplase and outcome in stroke: an updated pooled analysis of ECASS, ATLANTIS, NINDS, and EPITHET trials", Lancet, 2010, 375: 1695-703 (Year: 2010).*

International Search Report and Written Opinion for PCT/US20/29205. Mailed Jul. 6, 2020. 8 pages.

Extended European Search Report for 20795588.1 Mailed Feb. 5, 2023. 9 pages.

Adibhatla et al., Tissue plasminogen activator (tPA) and matrix metalloproteinases in the pathogenesis of stroke: therapeutic strategies. CNS Neurol Disord Drug Targets. Jun. 2008;7(3):243-53.

Badhiwala et al., Endovascular Thrombectomy for Acute Ischemic Stroke: A Meta-analysis. JAMA. Nov. 3, 2015;314(17):1832-43.

Campbell et al., Endovascular thrombectomy for stroke: current best practice and future goals. Stroke Vasc Neurol. Feb. 16, 2016;1(1):16-22.

Daffertshofer et al., Ultrasound in the treatment of ischaemic stroke. Lancet Neurol. May 2003;2(5):283-90.

Deng et al., Recombinant Tissue Plasminogen Activator-conjugated Nanoparticles Effectively Targets Thrombolysis in a Rat Model of Middle Cerebral Artery Occlusion. Curr Med Sci. Jun. 2018;38(3):427-435.

Evans et al., Revolution in acute ischemic stroke care: a practical guide to mechanical thrombectomy. Pract Neurol. Aug. 2017;17(4):252-265.

Gandhi et al., Neuroendovascular management of emergent large vessel occlusion: update on the technical aspects and standards of practice by the Standards and Guidelines Committee of the Society of NeuroInterventional Surgery. J Neurointerv Surg. Mar. 2018;10(3):315-320.

Goldstein. Acute ischemic stroke treatment in 2007. Circulation. Sep. 25, 2007;116(13):1504-14.

Goto et al., Neurotoxic effects of exogenous recombinant tissue-type plasminogen activator on the normal rat brain. J Neurotrauma. Apr. 2007;24(4):745-52.

Goyal et al., Analysis of Workflow and Time to Treatment and the Effects on Outcome in Endovascular Treatment of Acute Ischemic Stroke: Results from the Swift Prime Randomized Controlled Trial. Radiology. Jun. 2016;279(3):888-97.

Huttinger et al., Ferric Chloride-induced Canine Carotid Artery Thrombosis: A Large Animal Model of Vascular Injury. J Vis Exp. Sep. 7, 2018;(139):57981. 1-8.

Jaffer et al., Advances in stroke therapy. Drug Deliv Transl Res. Dec. 1, 2011;1(6):409-19.

Kalogeris et al., Mitochondrial reactive oxygen species: a double edged sword in ischemia/reperfusion vs preconditioning. Redox Biol. Jun. 2, 2014;2:702-14.

Kim et al., Treatment With Tissue Plasminogen Activator in the Golden Hour and the Shape of the 4.5-Hour Time-Benefit Curve in the National United States Get With The Guidelines—Stroke Population. Circulation. Jan. 10, 2017;135(2):128-139.

Li et al., Ferric chloride-induced murine carotid arterial injury: A model of redox pathology. Redox Biol. Jan. 26, 2013;1(1):50-5.

Nair et al., Biodegradable polymers as biomaterials. Progress in Polymer Science, 2007, 32 (8-9), 762-798.

Papanagiotou et al., Endovascular Thrombectomy in Acute Ischemic Stroke. Circ Cardiovasc Interv. Jan. 2018;11(1):e005362. 1-18.

Peters et al., Increased formation of reactive oxygen species after permanent and reversible middle cerebral artery occlusion in the rat. J Cereb Blood Flow Metab. Feb. 1998;18(2):196-205.

Petro et al., Tissue plasminogen activator followed by antioxidant-loaded nanoparticle delivery promotes activation/mobilization of progenitor cells in infarcted rat brain. Biomaterials, 2015, 81, 169-180.

Reddy et al., Superoxide dismutase-loaded PLGA nanoparticles protect cultured human neurons under oxidative stress. Appl Biochem Biotechnol. Dec. 2008; 151(2-3): 565-577.

Saver et al., Time to Treatment With Endovascular Thrombectomy and Outcomes From Ischemic Stroke: A Meta-analysis. JAMA. Sep. 27, 2016;316(12):1279-88.

Singhal et al., Nanoparticle-mediated catalase delivery protects human neurons from oxidative stress. Cell Death and Disease. 2013. 4, e903. 1-9.

Yepes et al., Tissue-type plasminogen activator induces opening of the blood-brain barrier via the LDL receptor-related protein. J Clin Invest. Nov. 2003;112(10):1533-40.

* cited by examiner

THROMBOLYTIC AND NEURO/VASCULOPROTECTIVE NANOCONJUGATES

The present application claims priority to U.S. Provisional application Ser. No. 62/837,980 filed Apr. 24, 2019, which is herein incorporated by reference in its entirety.

STATEMENT REGARDING FEDERAL FUNDING

This invention was made with government support under grant numbers 1R01NS113680-01, 1UH54HL119810-07, 1R01NS070896-01, awarded by the National Institutes of Health. The government has certain rights in the invention.

FIELD

Provided herein are compositions, systems, kits, and methods for treating a patient with a thromboembolism by administering nanoconjugates comprising nanoparticles encapsulating and/or conjugated to: i) tissue-type plasminogen activator (tPA), and ii) at least one antioxidant enzyme selected from the group consisting of: superoxide dismutase, glutathione peroxidase, glutathione reductase, and a catalase.

BACKGROUND

Thromboembolic stroke, the most common of acute ischemic strokes (85%; the remaining 15% are hemorrhagic), is the major cause of death and disability in the elderly. The estimated 680,000 new strokes per year in the US carry a mortality rate of 53-94%, with stroke-related costs totaling an estimated $34 billion a year. There are ~7 million people in the US with stroke related disability. The only US FDA-approved treatment for ischemic stroke—recombinant human tissue-type plasminogen activator (tPA)—has significant limitations, including a short time window for treatment, neurotoxicity, and a high propensity to aggravate reperfusion injury, particularly with delayed treatment. Conventionally, thrombolysis is achieved by administering tissue-type plasminogen activator (tPA). However, its use is limited to only few hours after embolism. Beyond this time window, tPA aggravates reperfusion injury due to increased oxidative stress that causes hemorrhage and further tissue damage. Further, t-PA is not very effective in platelet-rich clots (PRC). Within the fibrin network of a PRC clot, large platelet aggregates are observed. These aggregates lead to increased rigidity of the clot and significantly increase time to tPA-induced lysis compared with other clots which are rich in red blood cells (RBC). In addition, it is suggested that plasminogen activator inhibitor 1 (PAI-1) is released from platelets convey resistance of platelet-rich blood clots to thrombolysis. tPA acts by activating plasminogen activator. Confounding these issues, one recent study showed that tPA inhibits migration of circulating and neuronal progenitor cells (NPCs) in the infarcted brain, thus hindering the brain's endogenous repair mechanisms.

In recent clinical trials, another method, endovascular thrombectomy (EVT), in which clots are retracted using a "stent retriever" device, has shown to reduce disability and mortality, but EVT is limited to large-vessel occlusion (e.g., internal carotid artery or proximal middle cerebral artery) and it cannot prevent reperfusion injury, often requires tPA administration to dissolve fragmented clot and/or deep-tissue emboli, and its beneficial effects diminish substantially with each hour of delay beyond ~4.5 hr post stroke. EVT must be performed by trained neurointerventionalists under general anesthesia, and is associated with device related vessel injury. EVT can benefit a select patient population (an estimated 3-22% of stroke patients with large-vessel occlusion) in whom tPA alone is ineffective due to its short half-life (~5 min), which does not give enough contact time for tPA to cause lysis of a large clot. In a meta-analysis of eight high-quality randomized clinical trials, EVT and standard tPA treatment showed similar intracranial hemorrhage and mortality rates.

SUMMARY

Provided herein are compositions, systems, kits, and methods for treating a patient with a thromboembolism by administering nanoconjugates comprising nanoparticles encapsulating and/or conjugated to: i) tissue-type plasminogen activator (tPA), and ii) at least one antioxidant enzyme selected from the group consisting of: superoxide dismutase, glutathione peroxidase, glutathione reductase, and a catalase.

In some embodiments, provided herein are methods of treating a patient with a thromboembolism comprising: administering a composition to a subject (e.g., human subject) with a thromboembolism, wherein the composition comprises nanoparticles encapsulating and/or conjugated to: i) tissue-type plasminogen activator (tPA) (e.g., human tPA), and ii) at least one antioxidant enzyme selected from the group consisting of: superoxide dismutase, glutathione peroxidase, glutathione reductase, and a catalase. In certain embodiments, the subject has a thromboembolism in the brain.

In particular embodiments, provided herein are compositions comprising: nanoparticles encapsulating and/or conjugated to: i) tissue-type plasminogen activator (tPA), and ii) at least one antioxidant enzyme selected from the group consisting of: superoxide dismutase, glutathione peroxidase, glutathione reductase, and a catalase. In some embodiments, the compositions further comprise a sugar.

In certain embodiments, the nanoparticles further comprise an imaging agent. In other embodiments, the thromboembolism comprises a platelet-rich clot.

In certain embodiments, the nanoparticles comprise poly (D,L-lactide-co-glycolide) (PLGA) or other bio-compatible polymer. In some embodiments, the nanoparticles comprise pores. In further embodiments, the tPA is the full-length protein or a biologically fragment or variant thereof. In other embodiments, the tPA is conjugated to the nanoparticles. In further embodiments, the antioxidant enzyme or enzymes are encapsulated by the nanoparticles.

DESCRIPTION OF THE FIGURES

FIG. 1: Neuroprotective effect of a tPA nanoconjugate under oxidative stress as described in Example 1. Rat neurons (Gibco) were treated with $H_2O_2$ with/without different treatments. After 24 hours, cell viability was determined using MTT assay. Dose of nano-SOD/CAT or tPA nanoconjugate=200 µg/ml. Control=No $H_2O_2$; No treatment=cells exposed to $H_2O_2$ but given no treatment; remaining groups received both $H_2O_2$ and the respective treatments. Data as mean±s.e.m., n=6.

FIG. 2: Thrombolytic activity of the tPA nanoconjugate. Clot was prepared by collecting blood (0.5-1 ml) in a PE50 (ID. 0.58 mm OD. 0.965 mm) tube by inserting it into a tail vein following incision (1-1.5 cm long). Tube with blood was kept at 4° C. for the desired time period. Tube with clot was cut and flushed out using syringe filled with saline. Clots were treated with saline, tPA alone (dose=25 μg/ml or tPA nanoconjugate in 24-well plate at 37° C. for 30 min. Each mg of tPA nanoconjugate contains 25 μg tPA.

FIG. 4: Efficacy of tPA nanoconjugate in a stroke model. tPA nanoconjugate or tPA in solution (tPA) was administered IV 6 hr post stroke via tail vein injection. Survival and neurologic score were monitored at regular time intervals. Infarct volume was calculated at 30 days, when the study was terminated. A) Survival, B) Neurologic scoring, and C) Infarct volume. *$p \leq 0.001$ tPA nanoconjugate vs. tPA-sol or saline.$p=0.05$ tPA nanoconjugate vs. tPA-sol at 30 d; *$p=NS$ tPA nanoconjugate vs. tPA at 3 d. Data are shown as mean±s.e.m. n=20 to 45. Each mg of nano-SOD/CAT contained 25 μg tPA conjugated.

DETAILED DESCRIPTION

Provided herein are compositions, systems, kits, and methods for treating a patient with a thromboembolism by administering nanoconjugates comprising nanoparticles encapsulating and/or conjugated to: i) tissue-type plasminogen activator (tPA), and ii) at least one antioxidant enzyme selected from the group consisting of: superoxide dismutase, glutathione peroxidase, glutathione reductase, and a catalase.

Provided herein are tPA nanoconjugates which have dual-action as both a thrombolytic and a neuro-/vasculoprotectant for the treatment of, for example, thromboembolic stroke. The current sole US FDA-approved treatment for ischemic stroke is recombinant human tissue-type plasminogen activator (tPA), which has significant limitations such as a limited window for treatment, short half-life (5 minutes), neurotoxicity, and a high propensity to aggravate reperfusion injury. The nanoconjugates herein provides a formulation that solves at least some of these issues.

In certain embodiments, the tPA nanoconjugates provided herein are composed of tPA conjugated to nanoparticles loaded with antioxidant enzymes (e.g., superoxide dismutase (SOD) and catalase (CAT) (nano-SOD/CAT). As used herein, "tPA" includes both the full-length tPA protein (e.g., human tPA), as well as biologically active fragments or variants that have the same or similar activity of full length tPA). Such nanoconjugate can be used alone or in conjunction with EVT (endovascular thrombectomy) or another intervention (such as ultrasound).

In particular embodiments, the tPA nanoconjugates are more effective at lower doses than tPA alone due to the sustained thrombolysis of conjugated or encapsulated tPA. The nanoconjugate may be less toxic, since a smaller dose may be used to get the same thrombolytic effect of tPA alone. In certain embodiments, the tPA acts as a ligand for the nanoparticle to target areas of occlusion so that antioxidants which are loaded in nanoparticles are released where they are needed i.e. ischemic tissue. Such constructs are effective in dissolving an old clot, and platelet rich clots, since the conjugated tPA is more stable, has a longer half-life, and is able to sustain its effect in the body for a longer time than tPA alone.

The nanoconjugates provided herein have neuroprotectant and vasculoprotectant action as well. While the present invention is not limited to any particular mechanism, it is believed that the nanoconjugates facilitate neurogenesis/angiogenesis at, for example, the infarcted brain by promoting migration of progenitor/stem cells, thus affecting the brain's endogenous repair mechanism. This is an improvement to tPA-only therapy, which inhibits the brain's endogenous repair mechanisms. As a result, the nanoconjugate can be effective even in the case of delayed treatment due to its protective effect from reperfusion injury.

Considering the above issues and limitations associated with the current treatment options for stroke, the tPA nanoconjugates herein, in certain embodiments, comprise tPA conjugated to nanoparticles loaded with antioxidant enzymes, such as superoxide dismutase (SOD) and catalase (CAT) (nano-SOD/CAT). In certain embodiments, tPA nanoconjugate following intravenous injection localizes at an embolic site to dissolve clot as well protect the embolic tissue from ischemia/reperfusion injury. This dual action nanoconjugate can be used alone or in conjunction with EVT (or other intervention such as ultrasound, microbubbles+ultrasound), via either intravenous or intraarterial (localized injection facilitates recanalization as well as to protect the tissue from ischemia reperfusion). Also, in some embodiments, since t-PA is conjugated, it is less likely to diffuse into brain parenchyma to cause neurotoxicity as tPA alone does through the premetallized blood-brain barrier.

In certain embodiments, the tPA nanoconjugates herein are dual action therapeutics, designed to achieve both enhanced thrombolysis and vascular/tissue protection from ischemia/reperfusion injury. In particular embodiments, the tPA nanoconjugate is an injectable formulation containing antioxidant enzymes encapsulated in sustained release biodegradable/biocompatible nanoparticles (e.g., composed of polymers known in the art for nanoparticles designed for administration to a subject; see Nair et al., Progress in Polymer Science, 32 (8-9), 2007, 762-798, herein incorporated by reference in its entirety, particularly for the polymers taught therein) that are then conjugated to tPA. With antioxidant enzymes, the tPA nanoconjugate mitigates oxidative stress, protecting vascular and ischemic tissue from reperfusion injury. In work conducted during development of embodiments therein, the tPA nanoconjugates: a) demonstrated better thrombolytic effect than tPA, b) targeted thrombus following intravenous injection, and c) was significantly more effective in rat thromboembolic stroke model than tPA in achieving neurological recovery and improving survival even when administered at 6 hrs post embolism. It has been demonstrated that oxidative stress-free environment promotes endogenous vascular/tissue repair mechanism by facilitating migration and differentiation of progenitor/stem cells in the ischemic tissue.

Reactive oxygen species (ROS), the main mediators of ischemia/reperfusion injury, trigger the cascade of degenerative events that leads to increased vascular permeability due to breakdown of the blood-brain barrier (BBB), which is further aggravated by tPA, leading to hemorrhage and further tissue damage. Consequently, neutralizing ROS with efficient antioxidant enzyme delivery at the time of reperfusion would prevent the cascade and facilitate regeneration via endogenous repair mechanisms mediated by migration and proliferation of stem/progenitor cells under oxidative stress-free environment. The tPA nanoconjugates herein address the concern of ROS.

In certain embodiments, the tPA nanoconjugates are an injectable formulation containing antioxidant enzymes, superoxide dismutase (SOD) and catalase (CAT), encapsulated in biodegradable nanoparticles (nano-SOD/CAT) that are then conjugated to tPA. In particular embodiments, the tPA nanoconjugates are formulated using an FDA approved polymer, poly dl-lactide co-glycolide (PLGA) or other polymer suitable for in vivo use. In certain embodiments, the nanoparticles are formulated such that encapsulated enzymes are released slowly and in active form to neutralize excess ROS in the target area in a subject. This strategy is to enhance the "good" characteristic of tPA (i.e., its thrombolytic effect) while mitigating its "bad" characteristics (i.e., neurotoxicity, vascular permeability effect, and oxidative stress). In certain embodiments, the bound tPA in the tPA nanoconjugate will be less permeable through the compromised BBB in stroke condition, hence its neurotoxic effect will be substantially minimized. Further, the antioxidant effect of the tPA nanoconjugate would protect the BBB from oxidative stress and reperfusion injury. Indeed, work conducted herein shows that the tPA nanoconjugate: a) has markedly better thrombolytic effects than tPA alone when tested in vitro (¼ lower dose than tPA alone to cause complete clot lysis) and causes no tPA-associated neurotoxicity under conditions of oxidative stress, b) given via intravenous injection even with delayed 6 hr post stroke in thromboembolic rat model, effectively reduced infarct volume and significantly increased survival rate vs. tPA alone (85% vs. 20% at 4 wks), and c) tPA nanoconjugate treated animals achieved better neurological recovery than untreated or tPA alone treated animals. The efficacy of the tPA nanoconjugate is attributed to its ability to localize in the ischemic brain targeting the clot following IV injection, sustaining the effect of tPA and hence causing better thrombolysis than t-PA alone (tPA $t_{1/2}$~5 min), and antioxidant enzymes delivered in the ischemic tissue neutralizing excess ROS, thus protecting cerebrovascular tissue from reperfusion injury as well as promoting the endogenous repair mechanism in the ischemic tissue under oxidative stress free condition.

In particular embodiments, the tPA nanoconjugates provides some or all of the following advantages: i) a dual-action therapeutic agent—both as a thrombolytic and neuro-/vasculoprotective; ii) target specific effect as injected tPA conjugate localizes to the embolic area to cause thrombolysis (tPA effect) as well as protect the tissue from ischemia/reperfusion injury (antioxidant enzymes loaded in nanoparticles to neutralize free radicals); iii) minimize the neurotoxic effect of t-PA as the conjugated tPA will not freely diffuse to the parenchyma as does free tPA through the permeabilized blood-brain barrier, as the conjugate rather would remain in the lumen of the blood vessel to cause thrombolysis; iv) nanoparticles conjugated to tPA can potentially block the leakage of blood-brain barrier due to their immobilization along blood vessel wall, preventing edema formation; v) effective at lower doses than tPA to cause thrombolysis/sustains the effect of tPA when conjugated; vi) target the clot, tPA acting as a ligand; this has been shown both in vitro and in vivo in embolic stroke model; vii) effective in dissolving old clot (with time clot becomes hard and hence tPA alone is ineffective because of its short half-life ~5 min); tPA conjugated to nanoparticles is more stable and hence sustains its effect; viii) effective even with delayed treatment due to its protective effect from reperfusion injury; ix) facilitate neurogenesis/angiogenesis at the infarcted brain by promoting migration of progenitor/stem cells whereas tPA alone inhibits, thus affecting the brain's endogenous repair mechanism; x) improves survival and promotes better recovery than tPA alone, as tPA alone causes more mortality than untreated control; xi) less toxic due to reduced dosing needed to cause thrombolysis than tPA alone; xii) can be used alone or in conjunction with EVT (or other intervention such as ultrasound), via either intravenous or intraarterial injection, even for large-vessel occlusion because of its thrombolytic efficacy (better than tPA alone) and its ability to minimize the effect of reperfusion injury; xiii) broader application to treat thromboembolism in other organs (e.g., lung, kidney, heart) or embolism caused by devices such as catheters, stents, where the tissue damage is mediated via the same mechanism of ischemia/reperfusion (due to formation of excess reactive oxygen species, ROS); xiv) extend the window of treatment which with tPA is limited to 4.5 hrs and recommended to be 3 hours, thus limiting the number of patients that can benefit from tPA alone treatment to less than about 5%; xv) minimize the impact of reperfusion injury which is greater than due to ischemia by neutralizing free radicals formed, preventing permeation of vessels of blood-brain barrier and hence the edema formation; xvi) promote regeneration of infarcted tissue via endogenous repair mechanism (recruitment of progenitor/stem cells) and promoting their differentiation in oxidative stress-free condition; xvii) sustains the effect of tPA and hence effective at lower doses reduces toxicity; xviii) effective via systemic administration (intravenous) as well as localized delivery (e.g. carotid injection), and effective for large and small vessel occlusion; and xviv) better neurological recovery with time in animals treated with tPA nanoconjugate than with tPA or untreated control.

In certain embodiments, the antioxidant enzymes are conjugated to tPA itself in addition to, or rather than, being conjugated or encapsulated by the nanoparticle. In other embodiments, rather than employ a nanoparticle (or in addition to a nanoparticle) the tPA and the antioxidant enzymes are conjugated to a polymer (e.g., polyethylene glycol), for example, where tPA is near one end of the polymer and the antioxidant enzyme(s) are near the other end.

A general treatment protocol with the nanoconjugates herein that could be employed in certain embodiments is provided below in Table 1.

TABLE 1

| Product Properties | Generally Acceptable Result | Preferred Result |
| --- | --- | --- |
| Primary Indication | Thrombolysis | Thrombolysis |
| Patient Population | Stroke/patients with stroke >4.5 hrs//Other embolic conditions | Stroke/Other embolic conditions/high risk patients/patients with embolism beyond >4.5 hrs/use in conjunction with endovascular thrombectomy |

TABLE 1-continued

| Product Properties | Generally Acceptable Result | Preferred Result |
| --- | --- | --- |
| Treatment Duration | Acute | Acute |
| Delivery Mode | Intravenous | Intravenous/Intra-arterial/localized |
| Dosage Form | Parenteral | Parenteral |
| Regimen | 10% dose as bolus over 1 min and remaining as infusion over 60 min | 10% dose as bolus over 1 min and remaining as infusion over 60 min |
| Efficacy | tPA dose = 0.9 mg/kg<br>tPA nanoconjugate dose = 0.22 mg/kg (4-fold lower than tPA dose)<br>$t_{1/2}$ of tPA =~5 min<br>$t_{1/2}$ tPA nanoconjugate = 60 min<br>Partial dissolution of clot and resumption of blood flow<br>Recovery with time | tPA nanoconjugate dose~0.09 mg/kg (10-fold lower than tPA dose)<br>$t_{1/2}$ tPA nanoconjugate = 120-180 min<br>Complete dissolution of clot and full resumption of blood flow<br>Noticeable recovery within 1 wk |
| Risk/Side Effects | No hemorrhage, hypotension, pulmonary embolism, cholesterol embolism or abnormal heartbeats | No hemorrhage, hypotension, pulmonary embolism, cholesterol embolism or abnormal heartbeats, no change is blood parameters. |

In certain embodiments, the nanoconjugates are provided in formulation that is ready for immediate reconstitution in normal saline and intravenous administration as a bolus followed by slow infusion which is similar to how tPA is administered (e.g., 10% bolus and remaining over 1 hour slow infusion). In other embodiments, the formulations include at least one cryoprotectant (e.g., sugars such as glucose, trehalose, fructose, and sucrose) that can easily redisperse the tPA nanoconjugate, as well as help in its stability. In general, nanoparticles have a propensity to aggregate during lyophilization (drying step) which is generally the last step in the production process. These sugars are also commonly used to protect proteins and antibodies from aggregation during lyophilization. Sugars may be employed, for example, at a concentration range of 0 to 20% in proportion to the tPA nanoconjugate prior to lyophilization. The tPA nanoconjugate can be tested with and without sugars added, pre- and post-lyophilization, for mean particle size, size distribution, polydispersity index (a measure of aggregation), and zeta potential (a measure of surface charge).

In certain embodiments, various constructs of the tPA nanoconjugates (e.g., with various antioxidant enzymes; various polymers for the nanoparticles; conjugation vs. encapsulation of proteins, etc.) are tested for efficacy in dog model of acute stroke. One such model is the ferric chloride-induced embolic dog model [4; this reference is incorporated by reference herein]. It is a model of redox pathology [5] and mimics many aspects human acute stroke condition. In brief, embolism is induced by applying umbilical tape soaked in ferric chloride solution around a carotid artery. The occlusion is confirmed by measuring blood flow and angiography. The model when treated with tPA alone has been shown to cause hemorrhage and hence is considered suitable for testing the effectiveness of the tPA nanoconjugate as it is not anticipated to cause hemorrhage. An exemplary study could employ a total of 12 dogs, two groups, one group treated with tPA alone and other with the test tPA nanoconjugate. The treatment with thrombolytic agent begins 6 hours post-embolism and the study is terminated ~2 hrs post treatment so that there is enough time to see the effect of reperfusion injury. One could use a ¼ dose of tPA in the tPA nanoconjugate as compared to tPA alone treatment. The following parameter could be tested:

1) Resumption of blood flow: Recanalization of thrombus will be indicated from the change in blood flow. This is continuously monitored so that we will be able to determine the extent of blood flow resumption with time following each treatment. In addition, blood pressure will be monitored continuously since tPA alone treatment is known to cause hypotension. Based on work conducted during development of embodiments herein, the test tPA nanoconjugate is expected to resume blood flow more rapidly and to a greater extent than tPA only. In addition, angiography will be performed prior to the treatment and at the time of termination of the study to ensure that blood flow has resumed.
2) tPA half-life: Blood is collected at a regular interval time which is used to analyze tPA activity. It is believed that the half-life of tPA when give as the tPA nanoconjugate to be greater than tPA.
3) Changes in blood parameters: Blood analysis is performed to ensure that the tPA nanoconjugate does not cause any significant changes in blood parameters such as RBC, WBC, Platelet counts, etc. In addition, blood clotting time is determined.
4) Carotid artery and brain analysis: The harvested embolic carotid artery is analyzed for residual thrombus. This is analyzed by imaging cross section of the arteries to determine the relative area that is recanalized. The brain sections are analyzed for hemorrhage and infarct volume which will provide assessment of safety and efficacy of the tPA conjugate vs. tPA alone.
5) Dose of tPA nanoconjugate in dog: In rat embolic model study herein, we have use 30 mg/kg dose of the tPA nanoconjugate. Since different species have different body weight to surface area and metabolic activities, conversion factor (Km) factor is generally used to determine equivalent dose. This conversion method is also used for determining human dose from animal studies. Accordingly, the dose of the tPA nanoconjugate used in dog studies can be about ¼ the dose that was used in rat studies or 7.5 mg/kg. Each mg tPA nanoconjugate contains 25 µg tPA. Hence, the dose of tPA would be 187.5 µg/kg. Based on the Km factor, in humans the dose would be ½ the dose used in dogs or about, for example, 3.75 mg/kg tPA nanoconjugate, equivalent to ~90 μg/kg tPA. tPA alone dose in humans for acute ischemic stroke could be, for example, ~900 μg/kg. Thus, the dose of tPA with the tPA nanoconjugate in humans, for example, could be 10-fold lower than tPA alone dose.

EXAMPLES

Example 1 tPA Nanoconjugate Protects Neurons from Oxidative Stress

This Example describes construction and testing of nanoconjugates for use in vivo.

Material and Methods

Materials: Poly (d,l-lactide co-glycolide) (PLGA; 50:50, inherent viscosity of 0.76-0.94 dL/g) was purchased from LACTEL Absorbable Polymers (Birmingham, AL). Poly (vinyl alcohol) (PVA; 87-90% hydrolyzed, mol. wt. 30,000-70,000), Bovine Serum Albumin (BSA), Superoxide Dismutase (SOD) from bovine red blood cells with activity of ~3000 units/mg, Catalase (CAT) from bovine liver with activity of 2000-5000 units/mg, Dimethyl tartaric acid (DMT), and glucose were purchased from Sigma-Aldrich (St. Louis, MO). Chloroform of HPLC grade was obtained from Fisher Scientific (Pittsburgh, PA).

Formulation of Nano-SOD/CAT: To prepare nano-SOD/CAT, SOD- and CAT-loaded NPs (nano-SOD, nano-CAT) were prepared separately and mixed in 1:2 w/w ratio during the last processing steps as described below. These were formulated by a double water-in-oil-in-water (w/o/w) emulsion solvent-evaporation method as described previously (Petro et al., 2016; herein incorporated by reference in its entirety). In a typical preparation, the 1× batch of nano-SOD and 2× batches of nano-CAT were prepared simultaneously. To prepare nano-SOD, 12 mg SOD and 18 mg BSA were dissolved in 300 μL MQ water. To prepare 1× batch of nano-CAT, 8 mg CAT and 22 mg BSA were dissolved in 300 μL Milli-Q water. The enzyme solution prepared as above was emulsified into a polymer solution containing 81 mg PLGA (with 9 mg DMT) in 3 mL chloroform. The primary w/o emulsion was formed, first by vortexing for 1 min followed by sonication for 2 min on an ice bath using a stepped microtip probe at 40% power (Qsonica LLC, Model Q500, Newtown, CT). In the formulation, BSA was used as an inert bulking protein that also helps in the encapsulation of enzymes as well as protect them from interfacial activation (Reddy et al., 2008, Singhal A et al., 2013). DMT was used as an inert plasticizer and pore forming agent that prevents the accumulation of acidic oligomers within NPs that are formed as a result of polymer degradation. These acidic oligomers if remained entrapped in NPs can potentially denature proteins. Also, because DMT forms pores, it helps in the release of the encapsulated proteins in a sustained manner. The above w/o emulsion was emulsified into 18 mL of 3% w/v PVA solution in water, first by vortexing for 1 min followed by sonication as above for 4 min to form multiple (w/o/w) emulsion. The emulsion was stirred overnight (~18 hrs) on a magnetic stir plate at 1,000 rpm in a fume hood at room temperature with an airflow set at a face velocity of 200 feet/min (6,400 cm/min). The formed NP dispersion was stirred for an additional one hour in a desiccator under vacuum (at ~23 psi) to ensure the removal of chloroform. At this stage, 1× nano-SOD and 2× nano-CAT were mixed. The formulation of nano-SOD/CAT was recovered by ultracentrifugation at 30,000 rpm (82,000×g) (Optima XE-90 with a 50.2Ti rotor, Beckman Coulter, Brea, CA) for 30 min. The supernatant was discarded and the pellet was resuspended in autoclaved Milli-Q water (ASTM Type 1 water, EMD Millipore Super-Q Plus filtration system; EMD Millipore, Darmstadt, Germany). The above process of centrifugation and resuspension of NPs was repeated two times to remove excess PVA, as well as the unencapsulated BSA and enzymes. After a final re-suspension and sonication of the pellet as above, it was centrifuged at 1,000 rpm (216×g) for 10 min (Thermo Electron Sorvall Legend RT Plus, Thermo Scientific, Waltham, MA) to remove large aggregates, if any. The supernatant was collected to which glucose was added as a cryoprotectant (2% w/v of NP suspension, the volume of NP suspension=20 ml or ~1:4 w/w NPs to Glucose). Based on the doses of the formulation for each animal, appropriate aliquots of nano-SOD/CAT dispersion were made in pre-weighted cryovials (Nunc, Roskilde, Denmark) and then the samples in vials were frozen at −80° C. in a freezer and lyophilized using a Freezone 4.5 (Labconco, Kansas City, MO) for 2 days at 0.016 mBar and −55° C. The added glucose before lyophilization helps in re-dispersing nano-SOD/CAT in saline without requiring sonication before injecting to animals. To estimate the amount of nano-SOD/CAT in each vial, few representative vials containing only added glucose were lyophilized and weighted. The average difference in the weight was used to calculate nano-SOD/CAT amount in each vial. The vials were stored at −20° C. until used for animal studies.

Characterization of NPs: Size and zeta potential of nano-SOD/CAT were determined using NICOMP 380 ZLS (Particle Sizing Systems, Port Richey, FL). Measurements were made on the nano-SOD/CAT dispersions prepared by sonication as above at ~1 mg/ml in water. Nanoparticles containing antioxidant enzymes, either single or combination of enzymes is conjugated to tPA. This conjugation is currently achieved via EDC-NHS chemistry. Here is the method of conjugation. tPA is conjugated to nano-SOD/CAT using 1-ethyl-3-(3-dimethylaminopropyl) carbodiimide hydrochloride (EDC) and N-hydroxysuccinimide (NETS) conjugation chemistry. In brief, nano-SOD/CAT in 2-(N-morpholino)ethanesulfonic acid (MES) buffer (pH 6) following activation is reacted with 0.1 μM tPA (5.9 mg) for 2 hr at room temperature in PBS (pH 7.5). The resulting tPA-conjugated nano-SOD/CAT (tPA nanoconjugate) is then dialyzed at 4° C. overnight to remove any unreacted substrate. The percentage conjugation of tPA with nano-SOD/CAT is estimated from the standard plot of concentration of tPA vs. its amidolytic activity. The activity of tPA is determined using the chromogenic substrate S-2288 (Chromogenix, Bedford, MA).

It is noted that other conjugation methods that can be used as nanoparticles can be formulated with different polymer with —COOH or —NH$_2$ functional groups. For example, one can use NHS ester chemistry as shown below:

g-Acylisourea
Active Ester

Crosslinked Proteins + Isourea By-product

Carbodiimide Crosslinker

Figure 1:
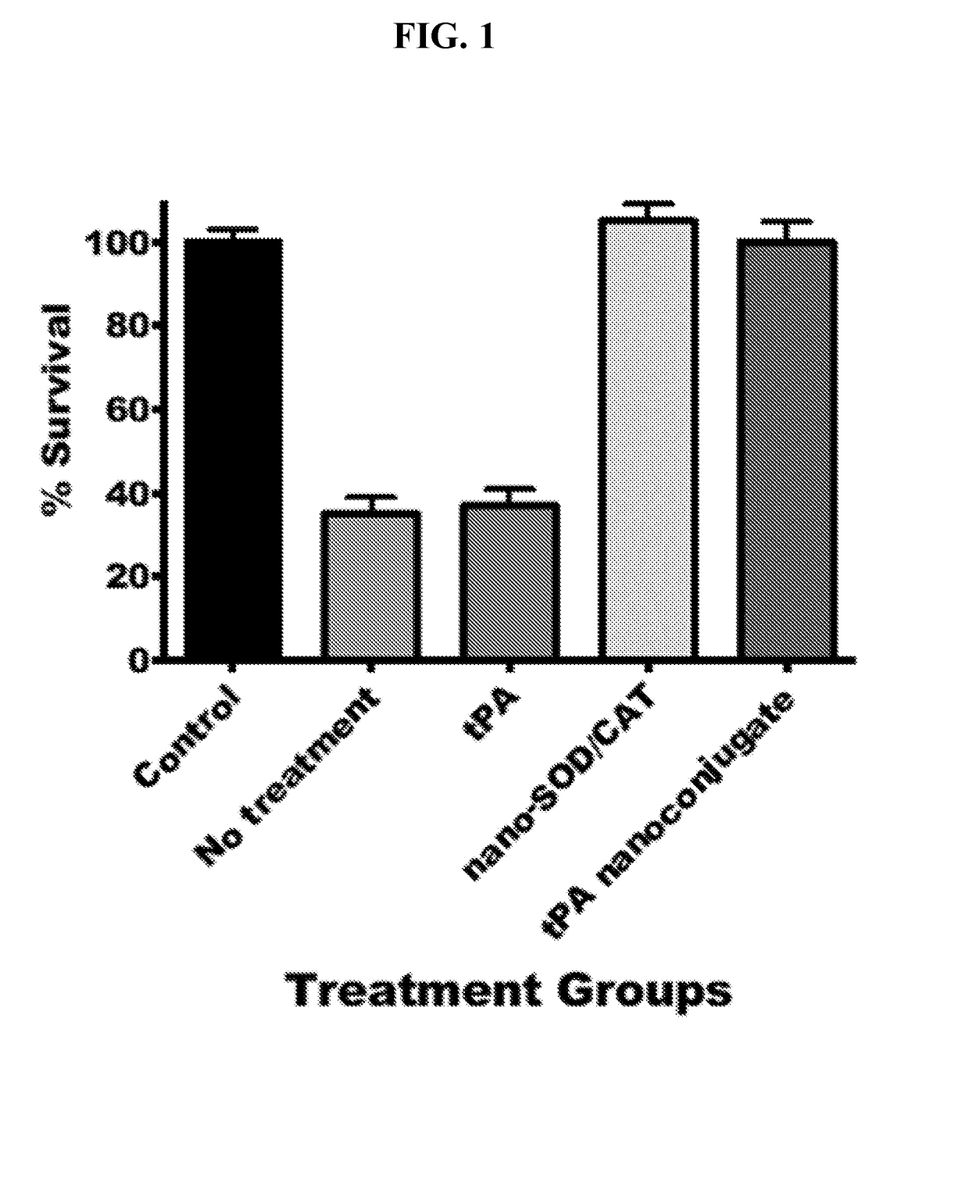

Results:

tPA Nanoconjugate Protects Neurons from Oxidative Stress: The tPA nanoconjugate shows the same neuroprotective efficacy as nano-SOD/CAT (without tPA) under $H_2O_2$-induced oxidative-stress conditions in rat neurons, confirming no adverse effect of the tPA when conjugated (FIG. 1).

Figure 2:
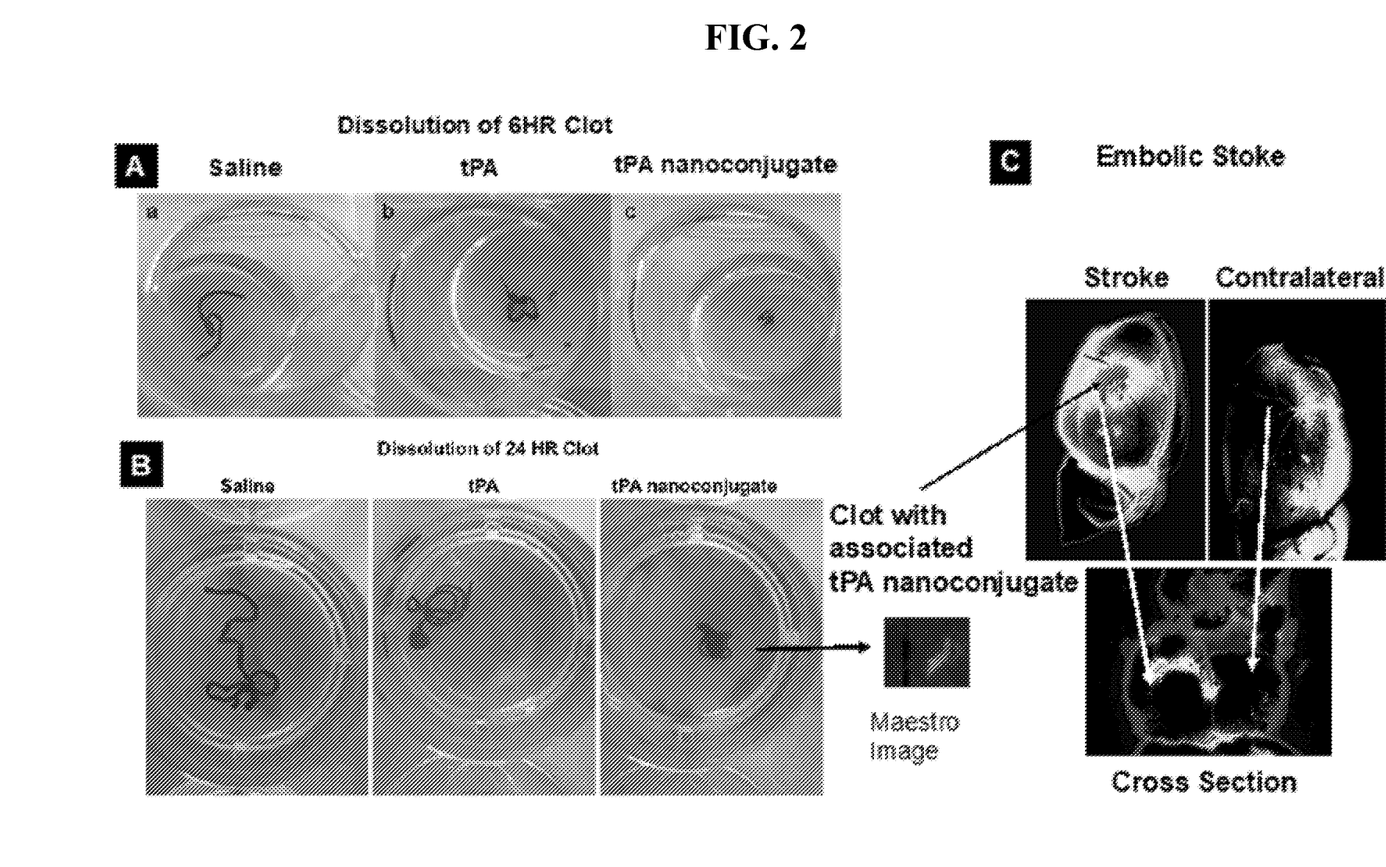
Figure 3:
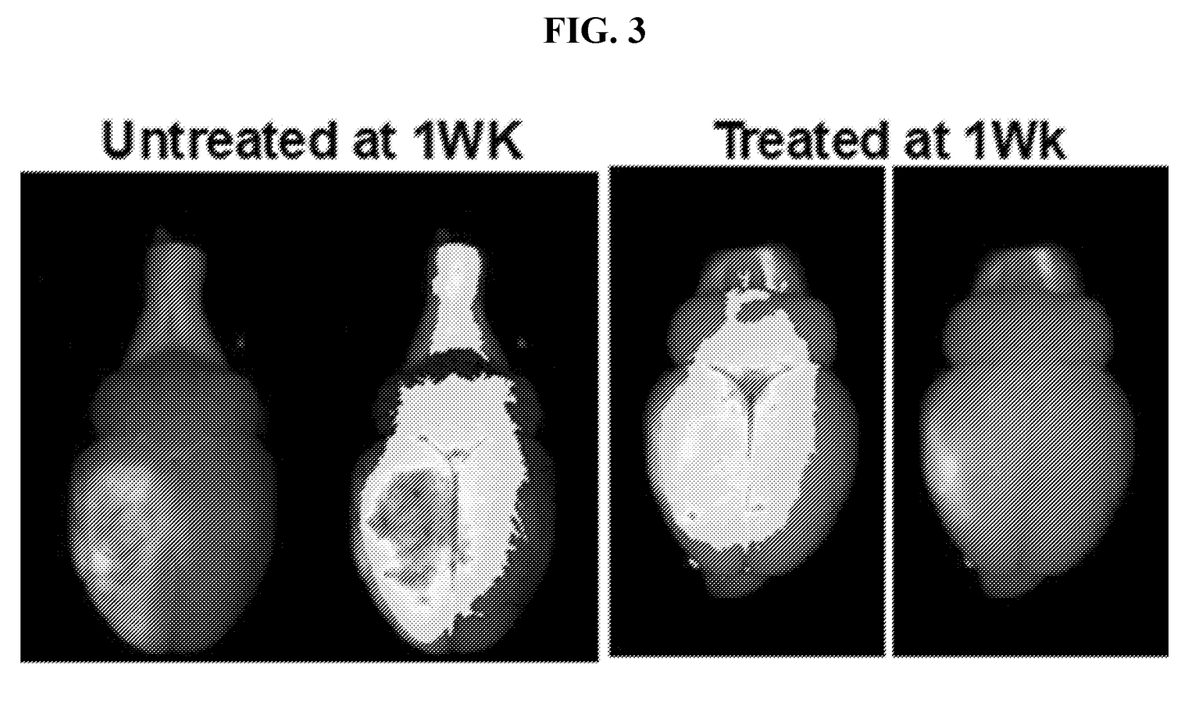
FIG. 3: Efficacy of the tPA nanoconjugate in embolic stroke model following IV injection. The tPA nanoconjugate was administered IV 6 hr after the stroke induction. Images shown are taken with Maestro at optimized wavelength. t-PA nanoconjugate-treated animals show significantly reduced infarct area vs. untreated control. Dose of tPA conjugate, 18 mg/kg, which is equivalent to ~400 μg tPA/kg.
Figure 4:
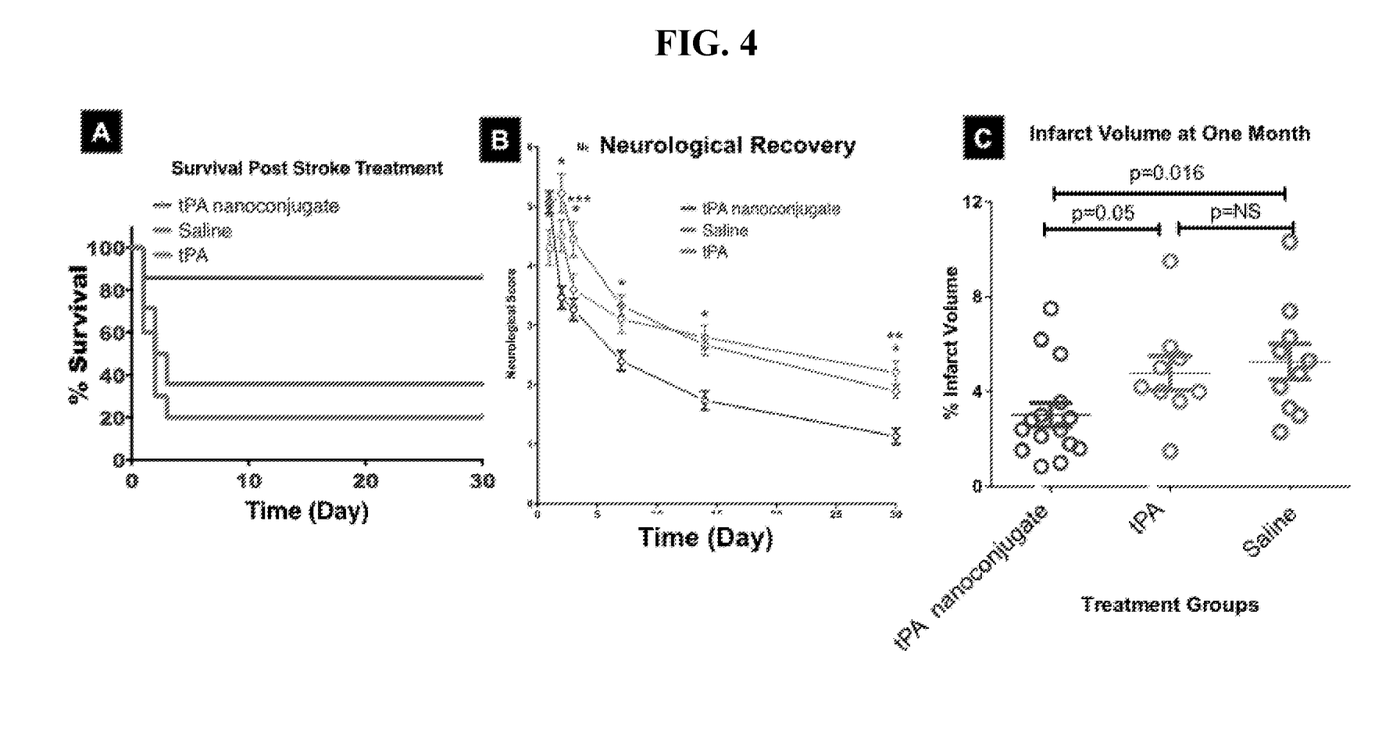

Thrombolytic Efficacy of tPA Nanoconjugate In Vitro: The clot that was ~6 hr old when incubated with the tPA nanoconjugate almost completely dissolved, even at ¼ of the dose used in the clot treated with tPA alone, which showed only partial clot dissolution (FIG. 2A). Following treatment, we observed first clot thinning and then coiling. The results indicate more rapid loss of fibrin support structure with time in the clot treated with the tPA nanoconjugate than in the clot given tPA alone. We then tested a clot that was 24 hr old and longer than that used previously and used near infrared (NIR) dye-loaded t-PA nanoconjugate (0.05% dye incorporated in nano-SOD/CAT prior to conjugation with tPA) so that its binding to the clot can be visualized. The clot treated with the tPA nanoconjugate was more coiled and much smaller than the clot treated with tPA alone (FIG. 2B). Optical imaging of the clot treated with the t-PA nanoconjugate showed a signal (clot as such does not show any signal in NIR), indicating its binding to the clot. To demonstrate that the tPA nanoconjugate indeed binds to the clot in vivo as well, we injected it via tail vein in a rat thromboembolic stroke model. The animal was euthanized and perfused, and the brain was harvested for optical imaging using Maestro optical system. The side of the brain that was occluded and the respective brain section showed a signal but not the contralateral side, demonstrating that the tPA nanoconjugate did bind to the clot, suggesting that the tPA bound to nano-SOD/CAT is acting as a ligand (FIG. 2C). Here NIR dye was used, but one could include other imaging/contrast agents (e.g. Gd, radiotracers, etc.).

tPA Nanoconjugate Reduces Infarct Size: The tPA nanoconjugate administered 6-hr post embolism was effective in reducing infarct volume when the brain was analyzed at 1-week post treatment as compared to untreated control (FIG. 3C).

tPA Nanoconjugate Improves Neurologic Recovery and Survival: The tPA nanoconjugate was shown to be significantly effective via IV injection administered at 6 hr post embolic stroke in improving survival (85% vs. 20% for tPA and 38% saline) (FIG. 4A) and neurologic recovery (FIG. 4B). The data also show significant reduction in infarct volume (calculated for the entire brain) when analyzed at the end of the study at 30 days post treatment (FIG. 4C). In the group treated with t-PA alone, mortality in most animals was determined to be due to hemorrhage and edema; many animals required early euthanasia due to uncontrolled seizure, breathing problem and deteriorating health, but such events were rare in animals receiving the tPA nanoconjugate.

Example 2

Treatment of a Platelet-Rich Clot

This Example describes construction of a platelet rich clot and testing the time it takes for tPA versus tPA nanoconjugates to dissolve such a clot.

The platelet rich clot (PRC) was prepared as follows. Five ml fresh blood is centrifuged at 180 relative centrifugal force (RCF) for 15 minutes to obtain 2.5 ml platelet-rich plasma which is then further centrifuged at 1500 RCF for 20 minutes. Supernatant 1.5 ml is removed and left platelets 0.8 ml is mixed with 0.2 ml 0.1M CaCl2 solution to get platelet rich clot. This is then filled into 60 cm PE60 tube and incubated at 37° C. for 2 hrs. The clot containing tubing is cut into different length segments.

Figure 5:
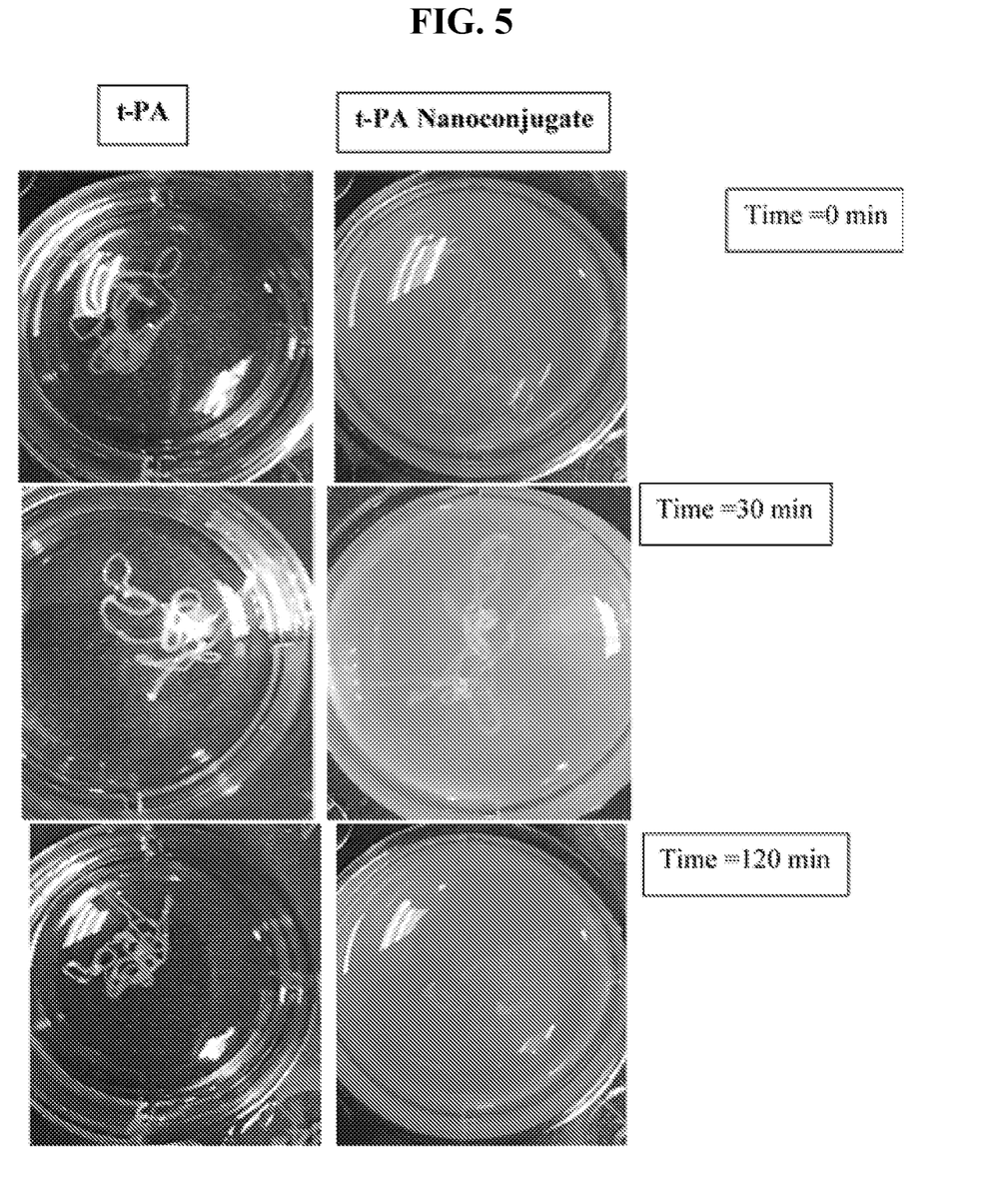
FIG. 5 demonstrates that the exemplary tPA nanoconjugates in Example 2 show almost complete fragmentation/dissolution of a platelet rich clot, whereas tPA only treatment shows intact clot at 120 minutes.

The clot from the tubing in pushed using saline into 6 well plates to test the effect of tPA nanoconjugate on its thrombolysis. The tPA nanoconjugates were composed of tPA conjugated to formulated as in Example 1. The clot in saline and thrombolytic agent is kept on a shaker maintained at 37° C. Serial time pictures were taken to determine time required to dissolve the clot. Results are shown in FIG. 5. Figures demonstrates that tPA nanoconjugates show almost complete fragmentation/dissolution of the platelet rich clot whereas tPA only treatment shows intact clot at 120 min

REFERENCES

1. Goldstein, L. B. Acute ischemic stroke treatment in 2007. Circulation 116, 1504-1514 (2007).
2. Kim, J. T., et al. Treatment With Tissue Plasminogen Activator in the Golden Hour and the Shape of the 4.5-Hour Time-Benefit Curve in the National United States Get With The Guidelines-Stroke Population. Circulation 135, 128-139 (2017).
3. Adibhatla, R. M. & Hatcher, J. F. Tissue plasminogen activator (tPA) and matrix metalloproteinases in the pathogenesis of stroke: therapeutic strategies. CNS Neurol Disord Drug Targets 7, 243-253 (2008).
4. Petro, M., et al. Tissue plasminogen activator followed by antioxidant-loaded nanoparticle delivery promotes activation/mobilization of progenitor cells in infarcted rat brain. Biomaterials 81, 169-180 (2016).
5. Campbell, B. C. V., Donnan, G. A., Mitchell, P. J. & Davis, S. M. Endovascular thrombectomy for stroke: current best practice and future goals. Stroke Vasc Neurol 1, 16-22 (2016).
6. Papanagiotou, P. & Ntaios, G. Endovascular Thrombectomy in Acute Ischemic Stroke. Circ Cardiovasc Interv 11, e005362 (2018).
7. Goyal, M., et al. Analysis of Workflow and Time to Treatment and the Effects on Outcome in Endovascular Treatment of Acute Ischemic Stroke: Results from the SWIFT PRIME Randomized Controlled Trial. Radiology 279, 888-897 (2016).
8. Saver, J. L., et al. Time to Treatment With Endovascular Thrombectomy and Outcomes From Ischemic Stroke: A Meta-analysis. JAMA 316, 1279-1288 (2016).
9. Gandhi, C. D., et al. Neuroendovascular management of emergent large vessel occlusion: update on the technical aspects and standards of practice by the Standards and Guidelines Committee of the Society of NeuroInterventional Surgery. J Neurointerv Surg 10, 315-320 (2018).
10. Evans, M. R. B., White, P., Cowley, P. & Werring, D. J. Revolution in acute ischaemic stroke care: a practical guide to mechanical thrombectomy. Pract Neurol 17, 252-265 (2017).
11. Badhiwala, J. H., et al. Endovascular Thrombectomy for Acute Ischemic Stroke: A Meta-analysis. JAMA 314, 1832-1843 (2015).
12. Daffertshofer, M. & Hennerici, M. Ultrasound in the treatment of ischaemic stroke. Lancet Neurol 2, 283-290 (2003).

and

[1] J. T. Kim, G. C. Fonarow, E. E. Smith, M. J. Reeves, D. D. Navalkele, J. C. Grotta, M. V. Grau-Sepulveda, A. F. Hernandez, E. D. Peterson, L. H. Schwamm, J. L. Saver, Treatment With Tissue Plasminogen Activator in the Golden Hour and the Shape of the 4.5-Hour Time-Benefit Curve in the National United States Get With The Guidelines-Stroke Population, Circulation, 135 (2017) 128-139.
[2] R. M. Adibhatla, J. F. Hatcher, Tissue plasminogen activator (tPA) and matrix metalloproteinases in the pathogenesis of stroke: therapeutic strategies, CNS Neurol Disord Drug Targets, 7 (2008) 243-253.
[3] M. Petro, H. Jaffer, J. Yang, S. Kabu, V. B. Morris, V. Labhasetwar, Tissue plasminogen activator followed by antioxidant-loaded nanoparticle delivery promotes activation/mobilization of progenitor cells in infarcted rat brain, Biomaterials, 81 (2016) 169-180.
[4] A. L. Huttinger, D. G. Wheeler, S. Gnyawali, D. Dornbos, J. M. Layzer, N. Venetos, S. Talentino, N. J. Musgrave, C. Jones, C. Bratton, M. E. Joseph, C. Sen, B. A. Sullenger, S. M. Nimjee, Ferric Chloride-induced Canine Carotid Artery Thrombosis: A Large Animal Model of Vascular Injury, J Vis Exp, September 7; (139). doi: 10.3791/57981 (2018).
[5] W. Li, T. M. McIntyre, R. L. Silverstein, Ferric chloride-induced murine carotid arterial injury: A model of redox-pathology, Redox Biology, 1 (2013) 50-55.
[6] B. C. V. Campbell, G. A. Donnan, P. J. Mitchell, S. M. Davis, Endovascular thrombectomy for stroke: current best practice and future goals, Stroke Vasc Neurol, 1 (2016) 16-22.
[7] J. L. Saver, M. Goyal, A. van der Lugt, B. K. Menon, C. B. Majoie, D. W. Dippel, B. C. Campbell, R. G. Nogueira, A. M. Demchuk, A. Tomasello, P. Cardona, T. G. Devlin, D. F. Frei, R. du Mesnil de Rochemont, O. A. Berkhemer, T. G. Jovin, A. H. Siddiqui, W. H. van Zwam, S. M. Davis, C. Castano, B. L. Sapkota, P. S. Fransen, C. Molina, R. J. van Oostenbrugge, A. Chamorro, H. Lingsma, F. L. Silver, G. A. Donnan, A. Shuaib, S. Brown, B. Stouch, P. J. Mitchell, A. Davalos, Y. B. Roos, M. D. Hill, H. Collaborators, Time to Treatment With Endovascular Thrombectomy and Outcomes From Ischemic Stroke: A Meta-analysis, JAMA, 316 (2016) 1279-1288.
[8] T. Kalogeris, Y. Bao, R. J. Korthuis, Mitochondrial reactive oxygen species: a double edged sword in ischemia/reperfusion vs preconditioning, Redox biology, 2 (2014) 702-714.
[9] O. Peters, T. Back, U. Lindauer, C. Busch, D. Megow, J. Dreier, U. Dirnagl, Increased formation of reactive oxygen species after permanent and reversible middle cerebral artery occlusion in the rat, Journal of Cerebral Blood Flow & Metabolism, 18 (1998) 196-205.
[10] M. Yepes, M. Sandkvist, E. G. Moore, T. H. Bugge, D. K. Strickland, D. A. Lawrence, Tissue-type plasminogen activator induces opening of the blood-brain barrier via the LDL receptor-related protein, J Clin Invest, 112 (2003) 1533-1540.

[11] H. Goto, H. Fujisawa, F. Oka, S. Nomura, K. Kajiwara, S. Kato, M. Fujii, T. Maekawa, M. Suzuki, Neurotoxic effects of exogenous recombinant tissue-type plasminogen activator on the normal rat brain, J Neurotrauma, 24 (2007) 745-752.

All publications and patents mentioned in the specification and/or listed below are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope described herein.

I claim:

1. A method of treating a patient with a stroke comprising: intravenously administering a composition to a subject who has had a stroke, wherein said intravenously administering occurs more than 4.5 hours after said stroke,
   wherein said composition comprises nanoparticles encapsulating tissue-type plasminogen activator (tPA), superoxide dismutase, and a catalase, and
   wherein said nanoparticles have pores and comprise PLGA and PVA.

2. The method of claim 1, wherein said tPA is the full-length protein or a biologically active fragment or variant thereof.

3. The method of claim 1, wherein said nanoparticles further comprise an imaging agent.

* * * * *

UNITED STATES PATENT AND TRADEMARK OFFICE
CERTIFICATE OF CORRECTION

| | | |
|---|---|---|
| PATENT NO. | : 12,409,147 B2 | Page 1 of 1 |
| APPLICATION NO. | : 17/605422 | |
| DATED | : September 9, 2025 | |
| INVENTOR(S) | : Vinod Labhasetwar | |

It is certified that error appears in the above-identified patent and that said Letters Patent is hereby corrected as shown below:

In the Specification

On Column 1, please replace the first paragraph as follows:
STATEMENT REGARDING FEDERAL FUNDING
This invention was made with government support under grant numbers NS113680, HL119810 and NS070896 awarded by the National Institutes of Health. The government has certain rights in the invention.

Signed and Sealed this
Ninth Day of December, 2025

John A. Squires
*Director of the United States Patent and Trademark Office*